United States Patent [19]

Krüger

[11] 4,449,972
[45] May 22, 1984

[54] STOMACH FLUSHING DEVICES

[76] Inventor: Christian Krüger, Curtiusstrasse 4,, 2400 Lübeck, Fed. Rep. of Germany

[21] Appl. No.: 406,512

[22] Filed: Aug. 9, 1982

[30] Foreign Application Priority Data

Aug. 29, 1981 [DE] Fed. Rep. of Germany ....... 3134251

[51] Int. Cl.³ ............................................ A61M 25/00
[52] U.S. Cl. ...................................... 604/96; 128/344
[58] Field of Search ........................ 604/96, 101, 103; 128/344, 129

[56] References Cited

U.S. PATENT DOCUMENTS

| | | | |
|---|---|---|---|
| 2,883,986 | 4/1959 | DeLuca et al. | 604/96 X |
| 3,459,175 | 8/1969 | Miller | 604/96 X |
| 4,328,056 | 5/1982 | Snooks | 604/96 X |

*Primary Examiner*—Stephen C. Pellegrino

*Attorney, Agent, or Firm*—Balogh, Osann, Kramer, Dvorak, Genova & Traub

[57] ABSTRACT

This invention provides a device for flushing and/or draining the stomach by means of a tube intended to be inserted through the oesophagus. A balloon in the form of a double-walled hollow cylinder elastically and hermetically encircles the tube periphery at a predetermined point in close contact with the same, and is releasably joined to the tube. The balloon is inflatable through a thin pipe extending to the proximal extremity of the tube.

Encircling terminal sections of the balloon are formed with increased thickness as compared to the remaining part of the balloon.

Prior to insertion of the tube into the oesophagus, the balloon is rolled up in the manner of a cuff on an obliquely-slotted sleeve which is slidable on to the tube, the balloon being thereafter unrolled from the sleeve to lie flat against the tube.

2 Claims, 4 Drawing Figures

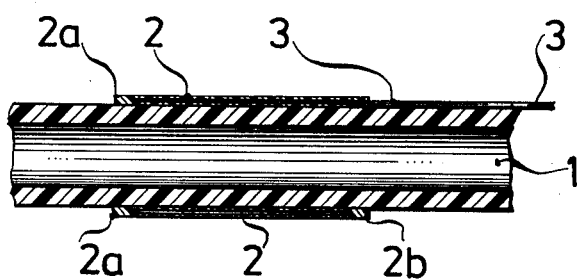
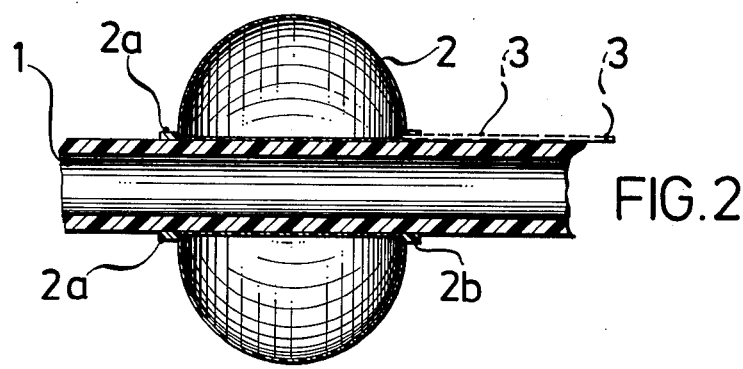
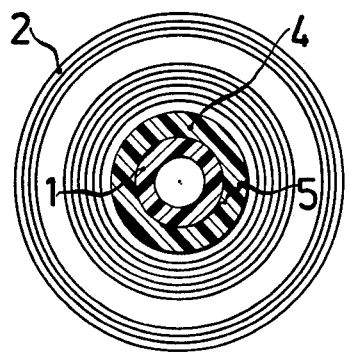
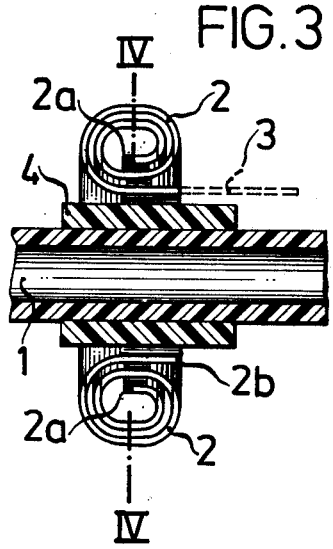

STOMACH FLUSHING DEVICES

BACKGROUND OF THE INVENTION

The present invention relates to devices for flushing and/or draining the stomach by means of a tube that is insertible into the stomach via the oesophagus.

In the case of poisoning by ingestion, a stomach flushing or draining operation is commonly first performed by means of a tube inserted into the stomach. In doing so the case may arise, which is not without risk to the patient, that parts of the stomach contents penetrate into the respiratory passages as a consequence of vomiting, if the epiglottis does not shut off the respiratory passages quickly enough due to intoxication and mechanical obstruction by the inserted tube.

It is of course possible to prevent an aspiration by means of intubation, which can be considered a current practice but intubation is frequently rejected by the patient in practice however and furthermore it is an operation which can only be performed in technically and implementally correct manner by qualified physicians.

It is an object of the invention to provide a device for flushing and/or draining the stomach, which may be applied in comparatively uncomplicated manner and with which the penetration of parts of the stomach contents into the respiratory passages following the insertion of the tube into the oesophagus or into the stomach is reliably prevented or minimised.

SUMMARY OF THE INVENTION

In accordance with the invention, this and other objects are attained by a device for the purpose hereinabove referred to, comprising a tube for introduction into the stomach through the oesophagus, and a balloon in the form of a double-walled hollow cylinder elastically and hermetically encircling said tube periphery at a predetermined point and in close contact therewith, said balloon being releasably joined to said tube and being inflatable through a thin pipe extending to the proximal extremity of said tube.

With a device of this kind, the oesophagus may be positively sealed off between the stomach and the epiglottis at an optionally predeterminable point by means of the inflated balloon, so that parts of the stomach contents cannot penetrate into the respiratory passages.

The insertion of the tube together with the balloon is possible without difficulty, since the balloon initially lies flat against the tube. In order that the balloon may first be located on the tube, the balloon may be rolled up in the form of a cuff on an obliquely-slotted sleeve capable of being slid on to the tube, said cuff having a substantially spiral cross-section, and the balloon may simply be unrolled again from the sleeve as soon as the unit comprising the sleeve carrying the balloon has been pushed to the preset position on the tube, the balloon being laid flat against the tube periphery in doing so. Following this, the cylindrical sleeve will be pulled out of the extremity of the balloon and off the tube. The tube may then finally be inserted together with the balloon and the balloon may be inflated thereupon to establish a secure seal between the tube and the adjacent portion of the oesophagus.

It should be possible to modify the internal diameter of the sleeve for adaptation to the existing external diameter of the tubes utilised, by expanding the cylindrical sleeve. In order that the sleeve diameter established by expanding the sleeve cannot vary, the mutually overlapping areas of the said oblique slot are denticulated, the teeth intermeshing in form-locked manner, such that a kind of ratchet joint is produced, which locks the sleeve against being constricted.

BRIEF DESCRIPTION OF THE DRAWINGS

In order that the invention may be more clearly understood, reference will now be made to the accompanying drawings which show certain embodiments thereof by way of example, and in which:

FIG. 1 shows a longitudinal cross-section through a part of the inventive device with the balloon lying flat against the tube, FIG. 2 shows an illustration corresponding to FIG. 1, but with the balloon inflated, FIG. 3 shows a longitudinal cross-section through a part of the device with an added sleeve member and with the balloon spirally rolled up on the sleeve in the form of a cuff, and FIG. 4 shows a cross-section through the embodiment shown in FIG. 3, along the section line IV—IV.

DETAILED DESCRIPTION OF THE PREFERRED EMBODIMENTS

Referring now to the drawings, at the time of introduction of a tube 1 into the oesophagus or into the stomach, a balloon 2 in the form of a double-walled hollow cylinder is pulled on to the tube flatly, elastically and tightly. The tube 2 has terminal sections 2a and 2b which are thickened or reinforced compared with the remaining part of the balloon material, so that they will lie against the tube periphery in commensurately stronger and tighter manner. This thickening may be obtained, for example, by welding together portions of the balloon material at the ends thereof. The balloon 2 may be inflated via a thin pipe 3 extending close to and along the tube 1 to its proximal extremity, the inflation being carried out for example by means of an injection syringe attached to the end of the thin pipe, but this has not been illustrated as it will be apparent to those skilled in the art, thus rendering illustration unnecessary.

In order to fit the balloon 2 so that it lies flat against the tube 1, a member comprising an elastic and obliquely-slotted sleeve 4 is taken and the annular balloon is rolled up in the form of a cuff on the sleeve 4 as shown in FIG. 3. This assembly is then pushed as a unit on to the tube. Prior to being pushed on however, the internal diameter of the sleeve 4 is matched to the external diameter of the tube 1, in such manner that the said unit may be conveyed to a preset point along the tube without obstruction. In order that the internal diameter of the sleeve 4 cannot be reduced whilst doing so, the mutually overlapping slot areas 5 have a detent denticulation (FIG. 4) which allows the sleeve to be expanded only, and furthermore does not allow of any reciprocal displacement of the mutually overlapping slot areas such as to constrict the sleeve. The interlocking teeth thus perform a kind of ratchet action.

After pushing the sleeve 4 on together with the balloon 2, the balloon is unwound or unrolled from the sleeve, the balloon being laid flat against the periphery of the tube 1 in doing so. Following this, the sleeve will be drawn off below the balloon extremity still encircling the same and stripped off the tube, so that the device shown in FIG. 1 and prepared for insertion is finally obtained. The tube may now be inserted into the stomach together with the balloon. The oesophagus is wholly sealed off with respect to the tube 1 by inflating the balloon (FIG. 2), so that the stomach contents may be removed only through the tube and whilst by-passing the respiratory passages.

What I claim is:

1. A device for flushing and/or draining a patient's stomach comprising a tube for introduction into the stomach through the oesophagus, and a balloon in the form of a double-walled hollow cylinder elastically and hermetically encircling said tube periphery at a predetermined point and in close contact therewith, said balloon being releasably joined to said tube and being inflatable through a thin pipe extending to the proximal extremity of said tube, including an obliquely-slotted sleeve member which is slidable on said tube, said balloon being rolled up in the manner of a cuff on said sleeve member prior to introduction through the oesophagus, said balloon being subsequently unrollable from said sleeve member to lie flat against said tube.

2. A device according to claim 1, wherein the internal diameter of said sleeve member is variable by expanding the sleeve member for adaptation to the external diameter of said tube and wherein the overlapping areas of said oblique slot are denticulated to lock said sleeve member against diminution of the preset sleeve diameter by a kind of ratchet action.

* * * * *